US010485994B2

(12) United States Patent
Kumata et al.

(10) Patent No.: US 10,485,994 B2
(45) Date of Patent: Nov. 26, 2019

(54) CHARGED PARTICLE BEAM TREATMENT APPARATUS

(71) Applicant: SUMITOMO HEAVY INDUSTRIES, LTD., Tokyo (JP)

(72) Inventors: Yukio Kumata, Tokyo (JP); Junichi Inoue, Ehime (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 212 days.

(21) Appl. No.: 15/717,647

(22) Filed: Sep. 27, 2017

(65) Prior Publication Data
US 2018/0015307 A1    Jan. 18, 2018

Related U.S. Application Data

(63) Continuation of application No. PCT/JP2016/055820, filed on Feb. 26, 2016.

(30) Foreign Application Priority Data

Mar. 30, 2015    (JP) .................................. 2015-069666

(51) Int. Cl.
*A61N 5/10*    (2006.01)

(52) U.S. Cl.
CPC ......... *A61N 5/1071* (2013.01); *A61N 5/1043* (2013.01); *A61N 5/1077* (2013.01); *A61N 2005/1087* (2013.01)

(58) Field of Classification Search
CPC .. A61N 5/1064; A61N 5/1065; A61N 5/1074; A61N 5/1075; A61N 5/1048; A61N 5/1077

(Continued)

(56) References Cited

U.S. PATENT DOCUMENTS 8,854,048 B2    10/2014    Otani et al.
9,312,100 B2    4/2016    Otani et al.
(Continued)

FOREIGN PATENT DOCUMENTS

JP    2005-124852 A    5/2005
JP    2012-083145 A    4/2012
(Continued)

OTHER PUBLICATIONS

International Search Report issued in Application No. PCT/JP2016/055820, dated May 10, 2016.

*Primary Examiner* — Samuel G Gilbert
(74) *Attorney, Agent, or Firm* — Michael Best & Friedrich LLP

(57) ABSTRACT

There is provided a charged particle beam treatment apparatus including an accelerator configured to emit a charged particle beam by accelerating a charged particle, an irradiation unit configured to irradiate an irradiation target with the charged particle beam, a beam transport line configured to transport the charged particle beam emitted from the accelerator, to the irradiation unit, a first dose measurement unit that is disposed inside the irradiation unit so as to measure a first dose of the charged particle beam, and a second dose measurement unit that is disposed in the beam trans port line so as to measure a second dose of the charged particle beam. A response frequency of the second dose measurement unit is higher than a response frequency of the first dose measurement unit.

4 Claims, 5 Drawing Sheets

(58) Field of Classification Search
USPC .............................................................. 600/1
See application file for complete search history.

(56) References Cited

U.S. PATENT DOCUMENTS

| | | | |
|---|---|---|---|
| 9,539,443 B2 * | 1/2017 | Slatkin | A61N 5/1064 |
| 2005/0087700 A1 | 4/2005 | Tadokoro et al. | |
| 2007/0147702 A1 | 6/2007 | Scoullar et al. | |
| 2007/0228305 A1 | 10/2007 | Keppel et al. | |
| 2008/0170663 A1 * | 7/2008 | Urano | A61N 5/1042 |
| | | | 378/65 |
| 2012/0305790 A1 | 12/2012 | Hanawa et al. | |
| 2012/0310030 A1 * | 12/2012 | Fontbonne | H01J 47/02 |
| | | | 600/1 |

FOREIGN PATENT DOCUMENTS

| | | |
|---|---|---|
| JP | 5022902 B2 | 6/2012 |
| JP | 5174005 B2 | 1/2013 |
| JP | 5463509 B2 | 4/2014 |
| WO | WO-2006/029475 A1 | 3/2006 |
| WO | WO-2007/126782 A2 | 3/2006 |
| WO | WO-2011/099448 A1 | 8/2011 |
| WO | WO-2012/120677 A1 | 9/2012 |

\* cited by examiner

CHARGED PARTICLE BEAM TREATMENT APPARATUS

RELATED APPLICATIONS

Priority is claimed to Japanese Patent Application No. 2015-069666, filed Mar. 30, 2015, and International Patent Application No. PCT/JP2016/055820, filed Feb. 26, 2016, the entire content of which is incorporated herein by reference.

BACKGROUND

Technical Field

A certain embodiment of the present invention relates to a charged particle beam treatment apparatus.

Description of Related Art

As a charged particle beam treatment apparatus which performs treatment by irradiating an irradiation target with a charged particle beam, a charged particle beam treatment apparatus disclosed in the related art is known, for example. The charged particle beam treatment apparatus disclosed in the related art irradiates and scans one layer set for the irradiation target with the charged particle beam in accordance with a predetermined scanning pattern. If the charged particle beam treatment apparatus completely irradiates one layer with the charged particle beam, the charged particle beam treatment apparatus changes energy of the charged particle beam, and performs irradiation while scanning the subsequent layer with the charged particle beam in accordance with a scanning pattern set for the subsequent layer.

SUMMARY

According to an embodiment of the present invention, there is provided a charged particle beam treatment apparatus including an accelerator configured to emit a charged particle beam by accelerating a charged particle, an irradiation unit configured to irradiate an irradiation target with the charged particle beam, a beam transport line configured to transport the charged particle beam emitted from the accelerator, to the irradiation unit, a first dose measurement unit that is disposed inside the irradiation unit so as to measure a first dose of the charged particle beam, and a second dose measurement unit that is disposed in the beam transport line so as to measure a second dose of the charged particle beam. A response frequency of the second dose measurement unit is higher than a response frequency of the first dose measurement unit.

DETAILED DESCRIPTION

Figure 1:
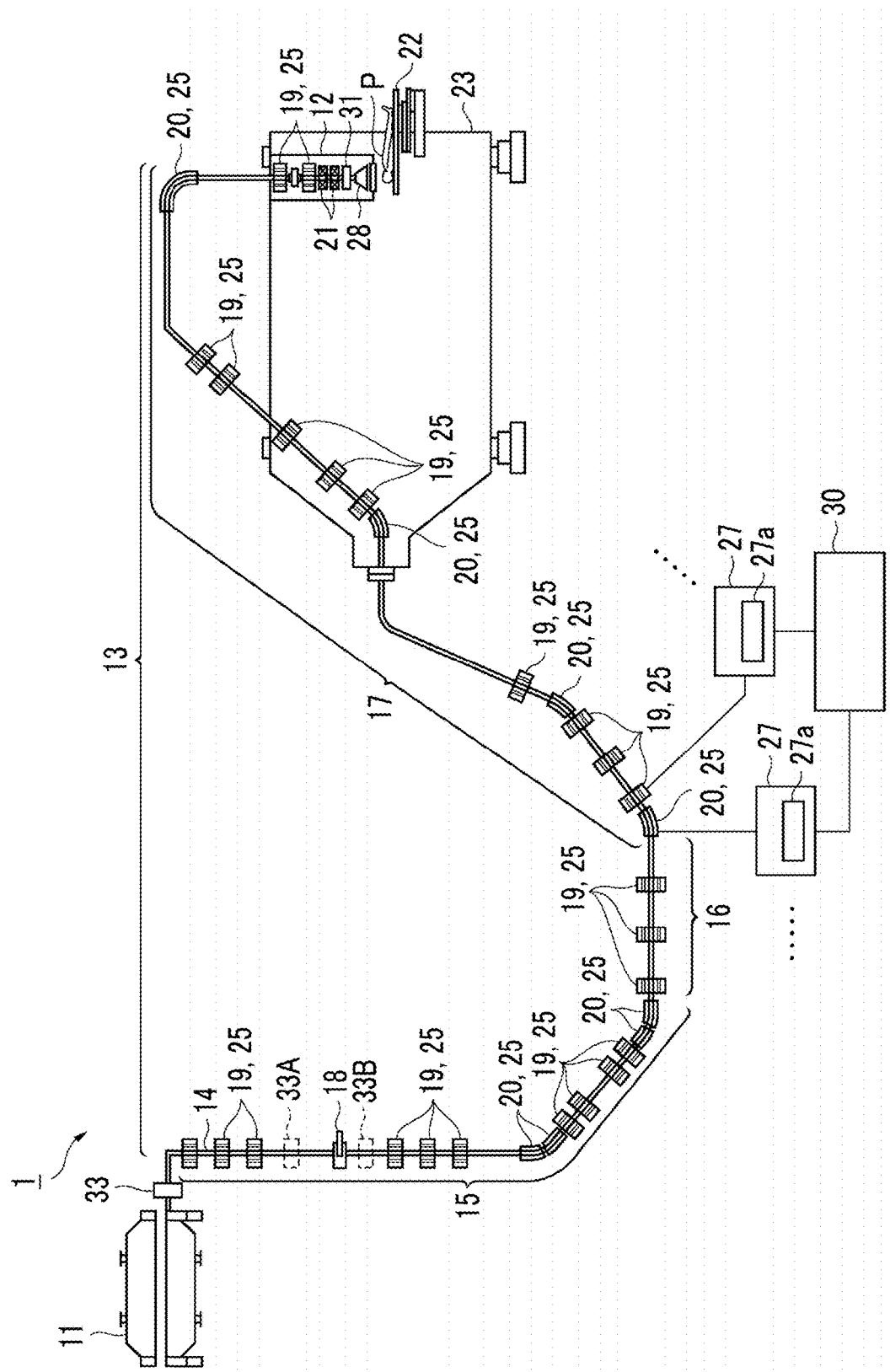
FIG. 1 is a schematic configuration diagram illustrating a charged particle beam irradiation apparatus according to an embodiment of the invention.

In recent years, a technique has been demanded in which the irradiation target is irradiated with the charged particle beam by performing scanning irradiation while scanning the beam with the charged particle beam at high speed. In this way, in order to perform the scanning irradiation while scanning the irradiation target with the charged particle beam at high speed, it is necessary to measure a dose (intensity) of the charged particle beam at high response speed. Herein, the charged particle beam treatment apparatus disclosed in the related art has a dose measurement unit that is disposed in an irradiation unit which irradiates the irradiation target with the charged particle beam. However, according to this dose measurement unit, there is a problem in that the dose is less likely to be measured at the high response speed.

It is desirable to provide a charged particle beam treatment apparatus capable of measuring a dose of a charged particle beam at high response speed.

In the charged particle beam treatment apparatus according to another aspect of an embodiment of the invention, the first dose measurement unit and the second dose measurement unit may include a pair of electrodes facing each other inside a space filled with gas, and a measurement unit configured to measure a current generated between the pair of electrodes. A distance between the pair of electrodes in the first dose measurement unit may be shorter than a distance between the pair of electrodes in the second dose measurement unit. According to this configuration, a simple configuration which merely reduces the distance between the pair of electrodes can increase the response frequency of the second dose measurement unit.

The charged particle beam treatment apparatus according to another aspect of an embodiment of the invention may further include a low pass filter configured to cut data relating to a frequency higher than a preset frequency from data measured by the first dose measurement unit, a high pass filter configured to cut data relating to a frequency lower than the preset frequency from data measured by the second dose measurement unit, and an ion source control unit configured to control an operation of an ion source which supplies an ion to the accelerator, based on a synthesized signal obtained by adding a signal output from the low pass filter and a signal output from the high pass filter to each other. According to this configuration, the first dose measurement unit whose response speed (response frequency) is low uses the low pass filter, thereby enabling measurement accuracy to be improved in a low frequency region (region having low response speed). The second dose measurement unit whose response speed (response frequency) is high uses the high pass filter, thereby enabling the measurement accuracy to be improved in a high frequency region (region having high response speed). The ion source control unit controls the operation of the ion source, based on the synthesized signal obtained by adding the signal output from the low pass filter and the signal output from the high pass filter to each other. Therefore, the ion source control unit can control the ion source, based on measurement results having the improved measurement accuracy in a wide range from the high frequency region to the low frequency region of the charged particle beam.

The charged particle beam treatment apparatus according to another aspect of an embodiment of the invention may further include an energy adjustment unit that is disposed in the beam transport line so as to adjust energy of the charged particle beam. The second dose measurement unit may be disposed on an upstream side from the energy adjustment unit. According to this configuration, the second dose measurement unit can measure the dose of the charged particle beam in a state of high energy before the energy of the charged particle beam is adjusted by the energy adjustment unit. Therefore, the measurement accuracy of the second dose measurement unit can be improved.

According to the embodiment of the invention, a dose of the charged particle beam can be measured at high response speed.

Hereinafter, an embodiment according to the invention will be described in detail with reference to the accompanying drawings. The terms "upstream" and "downstream" respectively mean upstream (an accelerator side) and downstream (a patient side) of a charged particle beam to be emitted.

As illustrated in FIG. 1, a charged particle beam treatment apparatus 1 is used for cancer treatment performed using radiotherapy. The charged particle beam treatment apparatus 1 includes an accelerator 11 that emits a charged particle beam by accelerating the charged particle and, an irradiation nozzle 12 (irradiation unit) that irradiates an irradiation target with the charged particle beam, a beam transport line 13 (transport line) that transports the charged particle beam emitted from the accelerator 11 to the irradiation nozzle 12, a second dose measurement unit 33 disposed in the beam transport line 13 so as to measure a dose of the charged particle beam, a degrader (energy adjustment unit) 18 disposed in the beam transport line 13 so as to adjust an emitting range of the charged particle beam by reducing energy of the charged particle beam, a plurality of electromagnets 25 disposed in the beam transport line 13, an electromagnet power source 27 disposed corresponding to each of the plurality of electromagnets 25, and a control unit 30 that controls the overall charged particle beam treatment apparatus 1. In the present embodiment, a cyclotron is employed as the accelerator 11. However, the present embodiment is not limited thereto. For example, the embodiment may employ other generation sources that generate the charged particle beam, such as a synchrotron (details will be described later with reference to FIG. 5), a synchrocyclotron, and a line accelerator.

The charged particle beam treatment apparatus 1 irradiates a tumor (irradiation target) of a patient P lying on a treatment table 22 with the charged particle beam emitted from the accelerator 11. The charged particle beam is obtained by accelerating a particle having an electric charge at high speed. For example, the charged particle beam is a proton beam or a heavy particle (heavy ion) beam. The charged particle beam treatment apparatus 1 according to the present embodiment irradiates the irradiation target with the charged particle beam by using a so-called scanning method. The irradiation target is virtually divided (sliced) in a depth direction, and each sliced plane (layer) is irradiated with the charged particle beam for an irradiation range on the layer.

An example of an irradiation method using the scanning method includes spot-type scanning irradiation and raster-type scanning irradiation. According to the spot-type scanning irradiation, if one spot is completely irradiated with the charged particle in the irradiation range of one layer, irradiation with the charged particle beam is stopped once. After the subsequent spot is fully prepared for irradiation, the subsequent spot is irradiated with the charged particle beam. On the other hand, according to the raster-type scanning irradiation, the irradiation range on one layer is continuously irradiated with the charged particle beam without intermediately stopping the irradiation. In this way, according to the raster-type scanning irradiation, the irradiation range on one layer is continuously irradiated with the charged particle beam. Therefore, unlike the spot-type scanning irradiation, the irradiation range in the raster-type scanning irradiation is not configured to include a plurality of spots. Hereinafter, an example will be described in which the irradiation is performed using the raster-type scanning irradiation. However, without being limited thereto, the present embodiment may adopt a configuration in which the irradiation is performed using the spot-type scanning irradiation.

The irradiation nozzle 12 is attached to the inside of a rotating gantry 23 rotatable around the treatment table 22 as large as 360 degrees, and is movable to any optional rotation position by the rotating gantry 23. The irradiation nozzle 12 includes a converging electromagnet 19, a scanning electromagnet 21, a first dose measuring unit 31, and a vacuum duct 28. The scanning electromagnet 21 is disposed in the irradiation nozzle 12. The scanning electromagnet 21 has an X-direction scanning electromagnet which performs scanning using the charged particle beam in an X-direction on a plane intersecting an irradiation direction of the charged particle beam, and a Y-direction scanning electromagnet which performs scanning using the charged particle beam in a Y-direction intersecting the X-direction on the plane intersecting the irradiation direction of the charged particle beam. The charged particle beam used in scanning by the scanning electromagnet 21 is deflected in the X-direction and/or the Y-direction. Accordingly, a diameter of the vacuum duct 28 located on a downstream side from the scanning electromagnet is expanded toward the downstream side. The first dose measurement unit 31 measures a dose of the charged particle beam before irradiation is performed (details will be described later).

The beam transport line 13 has a vacuum duct 14 through which the charged particle beam passes. The vacuum duct 14 is internally maintained in a vacuum state, thereby restraining the charged particle configuring the charged particle beam from being scattered during transportation.

The beam transport line 13 has an energy selection system (ESS) 15 which selectively extracts the charged particle beam having an energy width narrower than a predetermined energy width from the charged particle beam emitted from the accelerator 11 and having the predetermined energy width, a beam transport system (BTS) 16 which transports the charged particle beam having the energy width selected by the ESS 15 in a state where energy of the particle beam is maintained, and a gantry transport system (GTS) 17 which transports the charged particle beam from the BTS 16 toward the rotating gantry 23.

Figure 4:
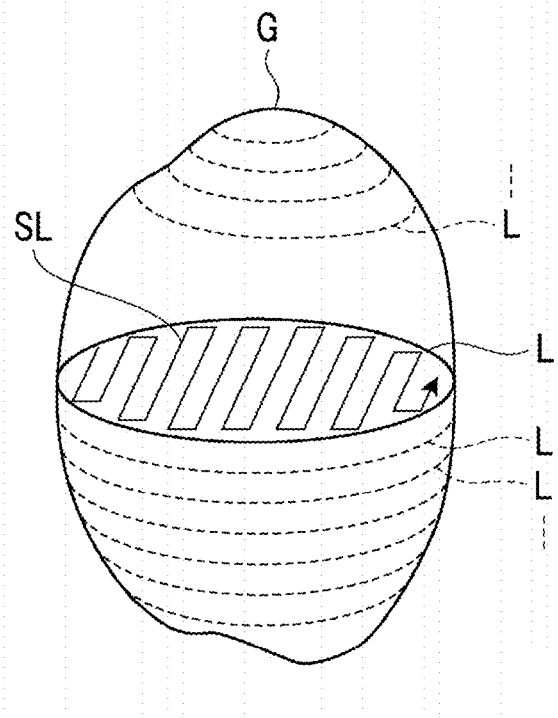
FIG. 4 is a schematic diagram illustrating a state where an irradiation target is virtually sliced.

The degrader 18 adjusts an emitting range of the charged particle beam by reducing the energy of the charged particle beam passing therethrough. A depth from a patient's body surface to a tumor serving as an irradiation target differs depending on each patient. Accordingly, when the patient is irradiated with the charged particle beam, it is necessary to adjust the emitting range which represents an arrival depth of the charged particle beam. The degrader 18 adjusts the energy of the charged particle beam emitted with constant energy from the accelerator 11, thereby adjusting the energy so that the charged particle beam properly reaches the irradiation target located at a predetermined depth inside the patient's body. The degrader 18 adjusts the energy of the charged particle beam for each layer obtained by virtually slicing the irradiation target. For example, as illustrated in FIG. 4, an irradiation target G is virtually sliced into a plurality of layers L. If one layer L is completely scanned with the charged particle beam (drawing a scanning line SL), the other layer L adjacent to one layer L is scanned with the charged particle beam.

A plurality of electromagnets 25 are disposed in the beam transport line 13, and adjust the charged particle beam so that the charged particle beam can be transported using a magnetic field by the beam transport line 13. As the electromagnets 25, the present embodiment employs the converging electromagnet 19 for converging a beam size of the charged particle beam during transportation, and the bending electromagnet 20 for bending the charged particle beam. Hereinafter, in some case, the converging electromagnet 19 and the bending electromagnet 20 are collectively referred to as the electromagnet 25 without distinction therebetween. The plurality of electromagnets 25 are also disposed on the downstream side from the degrader 18 in at least the beam transport line 13. However, in the present embodiment, the electromagnets 25 are disposed on the upstream side from the degrader 18. Here, as the electromagnet 25, the converging electromagnet 19 is also disposed on the upstream side from the degrader 18 in order to converge the beam size of the charged particle beam before the energy is adjusted by the degrader 18. The total number of the electromagnets 25 can be flexibly changed depending on a length of the beam transport line 13. For example, the number is approximately 10 to 40. FIG. 1 illustrates only some of the electromagnet power sources 27. However, in actual, the electromagnet power sources 27 are disposed therein as many as the electromagnets 25.

Each position of the degrader 18 and the electromagnet 25 in the beam transport line 13 is not particularly limited. In the present embodiment, the degrader 18, the converging electromagnet 19, and the bending electromagnet 20 are disposed in the ESS 15. The converging electromagnet 19 is disposed in the BTS 16, and the converging electromagnet 19 and the bending electromagnet 20 are disposed in the GTS 17. The degrader 18 is disposed in the ESS 15 located between the accelerator 11 and the rotating gantry 23 as described above. More specifically, the degrader 18 is disposed on the accelerator 11 side (upstream side) from the rotating gantry 23 in the ESS 15.

The electromagnet power source 27 generates a magnetic field of the electromagnet 25 by supplying a current to the corresponding electromagnet 25. The electromagnet power source 27 can set strength of the magnetic field of the corresponding electromagnet 25 by adjusting the current supplied to the corresponding electromagnet 25. The electromagnet power source 27 adjusts the current supplied to the electromagnet 25 in accordance with a signal output from the control unit 30. The electromagnet power sources 27 are disposed so as to respectively correspond to each electromagnet 25 one by one. That is, the electromagnet power sources 27 are disposed as many as the electromagnets 25. The electromagnet power source 27 has a storage unit 27a for storing a parameter of the electromagnet 25 corresponding to each layer.

A relationship between the depth of each layer of the irradiation target and the current supplied to the electromagnet 25 is as follows. That is, based on the depth of each layer, the energy of the charged particle beam which is needed to irradiate each layer with the charged particle beam is determined, and the energy amount adjusted by the degrader 18 is determined. Here, if the energy of the charged particle beam is changed, the strength of the magnetic field which is needed to bend and converge the charged particle beam is also changed. Therefore, the current supplied to the electromagnet 25 is determined so that the strength of the magnetic field of the electromagnet 25 is the strength corresponding to the energy amount adjusted by the degrader 18.

Figure 2:
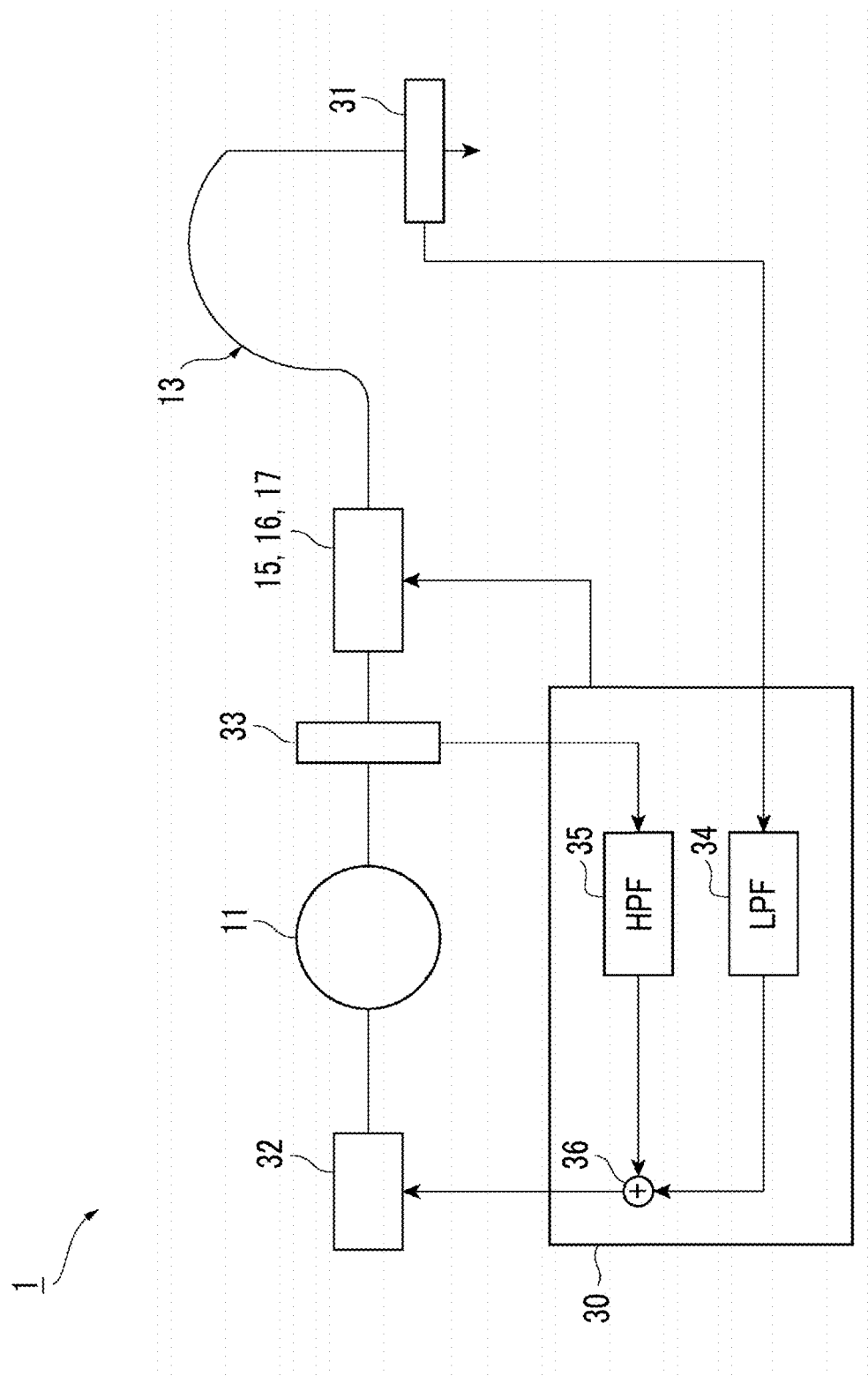
FIG. 2 is a schematic configuration diagram illustrating a main portion of the charged particle beam irradiation apparatus according to the present embodiment.

Next, referring to FIG. 2, a main portion of the charged particle beam treatment apparatus 1 according to the present embodiment will be described. In FIG. 2, the accelerator 11, the first dose measurement unit 31, the second dose measurement unit 33, the beam transport line 13, and the control unit 30 are illustrated in the charged particle beam treatment apparatus 1. In FIG. 2, the ESS 15, the BTS 16, and the GTS 17 are collectively illustrated as one block. FIG. 2 illustrates an ion source 32 which supplies an ion to the accelerator 11.

Figure 3:
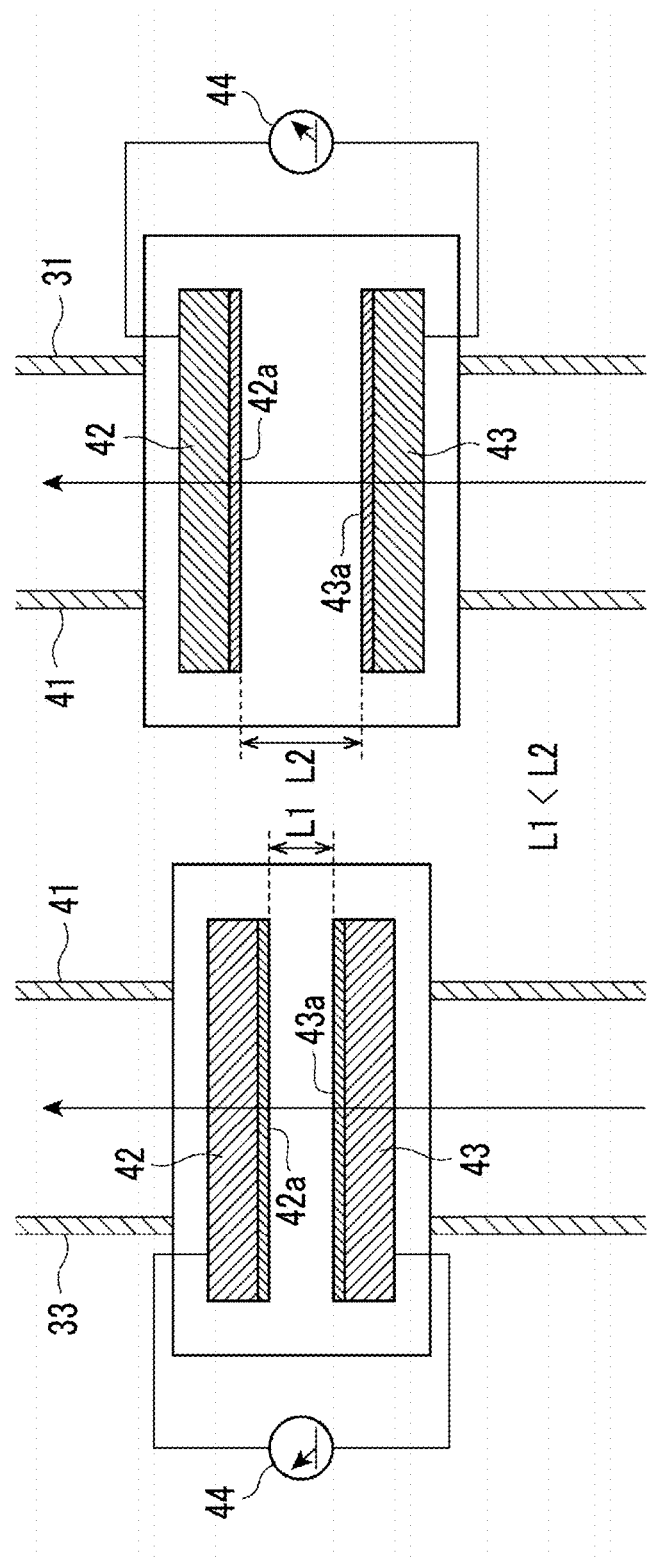
FIG. 3 is a schematic configuration diagram of a dose measurement unit.

Here, referring to FIG. 3, a configuration of the first dose measurement unit 31 and the second dose measurement unit 33 will be described in detail. The dose measurement units 31 and 33 are respectively configured to include an ionization chamber. Specifically, the dose measurement units 31 and 33 include a pair of electrodes 42 and 43 facing each other inside a space of a box 41 filled with gas (air or nitrogen), and a measurement unit 44 which measures a current generated between the pair of electrodes 42 and 43.

The electrodes 42 and 43 are configured to include a thin metal plate made of copper, for example. Facing surfaces thereof are covered with films 42a and 43a. A power source is connected between the electrodes 42 and 43, and a high voltage electric field is applied thereto. According to this configuration, if the charged particle beam passes through the inside of the dose measurement units 31 and 33, the charged particle beam collides with a molecule of a gas body, and the gas body is ionized. The electric field is applied between the electrodes 42 and 43. Accordingly, an ionized electron e– is focused on the electrode 43 on one side, and an ion i+ is focused on the electrode 42 having high pressure. The number of ionized electrons e– and ions i+ is proportional to a dose of the charged particle beam passing therethrough. Therefore, the dose of the charged particle beam is measured by a current value measured by the measurement unit 44.

A distance (distance indicated by L1 in FIG. 3) between the pair of electrodes 42 and 43 in the second dose measurement unit 33 is shorter than a distance (distance indicated by L2 in FIG. 3) between the pair of electrodes 42 and 43 in the first dose measurement unit 31. Compared to the second dose measurement unit 33, the first dose measurement unit 31 has a shorter distance between the pair of electrodes 42 and 43, and electrons can be focused thereon within a short time. Therefore, response speed (response frequency) of the second dose measurement unit 33 is higher than response speed (response frequency) of the first dose measurement unit 31. The distance between the pair of electrodes 42 and 43 in the first dose measurement unit 31 is set to 5 to 8 µm, and the response frequency is set to 1 kHz or lower (or lower than 1 kHz). The distance between the pair of electrodes 42 and 43 in the second dose measurement unit 33 is set to 4 µm or lower, and the response frequency is set to 1 kHz or higher (or lower than 1 kHz). The "response frequency" represents the number of times enabling a dose per unit time to be detected.

Referring back to FIG. 2, the control unit 30 has a function to control the overall charged particle beam treatment apparatus 1. Based on measurement results of the first dose measurement unit 31 and the second dose measurement unit 33, the control unit 30 controls a dose (intensity) of the charged particle beam emitted from the irradiation nozzle 12 so as to irradiate the irradiation target. In the present embodiment, the control unit 30 includes a low pass filter 34, a high pass filter 35, and an ion source control unit 36.

Specifically, the low pass filter 34 is electrically connected to the first dose measurement unit 31. The low pass filter 34 cuts data relating to a frequency higher than a preset frequency from data measured by the first dose measurement unit 31. A signal passing through the low pass filter 34 is output to the ion source control unit 36. A setting frequency of the low pass filter 34 may be set to 1 kHz or lower (or lower than 1 kHz).

The high pass filter 35 is electrically connected to the second dose measurement unit 33. The high pass filter 35 cuts data relating to a frequency lower than a preset frequency from data measured by the second dose measurement unit 33. A signal passing through the high pass filter 35 is output to the ion source control unit 36. A setting frequency of the high pass filter 35 may be set to 1 kHz or higher (or lower than 1 kHz).

The ion source control unit 36 is electrically connected to the low pass filter 34, the high pass filter 35, and the ion source 32. The ion source control unit 36 generates a synthesized signal obtained by adding the signal output from the low pass filter 34 and the signal output from the high pass filter 35 to each other. The ion source control unit 36 controls (feedback control) an operation of the ion source 32, based on the generated synthesized signal. For example, based on the synthesized signal, the ion source control unit 36 determines whether or not the dose of the charged particle beam satisfies a treatment plan. In a case where the ion source control unit 36 determines that the dose of the charged particle beam is insufficient, the ion source control unit 36 increases the ion amount supplied from the ion source 32. In a case where the ion source control unit 36 determines that the dose of the charged particle beam is excessive, the ion source control unit 36 decreases the ion amount supplied from the ion source 32.

Next, an operation effect of the charged particle beam treatment apparatus 1 according to the present embodiment will be described.

Here, in the charged particle beam treatment apparatus in the related art, the irradiation using the charged particle beam is controlled in accordance with the movement of the irradiation target moved by respiration of a patient. For example, the movement of the patient or the irradiation target is detected by X-ray CT or a laser measuring instrument, and a position to be irradiated with the charged particle beam is adjusted in accordance with the detected movement (movement amount). When the position to be irradiated with the charged particle beam is adjusted, the amount of excitation of a scanning electromagnet for scanning using the charged particle beam is adjusted. The movement of the irradiation target moved due to the respiratory motions varies with the lapse of time. Consequently, the irradiation position of the charged particle beam is less likely to be accurately adjusted. Accordingly, in a case where the charged particle beam is controlled in synchronization with respiration of the patient as described above, there is a problem in that the control becomes complicated. On the other hand, in a case where the irradiation timing is not controlled in synchronization with respiration, it is conceivable to irradiate the patient with the charged particle beam while the patient stops respiration. However, in a case where the scanning irradiation takes time, the patient has to stop breathing. Accordingly, in some cases, the burden on the patient may increase. Therefore, it is necessary to reduce the burden on the patient while treatment is performed on the patient by using the charged particle beam treatment apparatus. In order to reduce the burden on the patient, it is necessary to perform fast scanning irradiation. Consequently, it is necessary to measure the dose of the charged particle beam at high response speed.

Therefore, according to the charged particle beam treatment apparatus 1 in the present embodiment, the first dose measurement unit 31 is disposed inside the irradiation nozzle 12, and can measure the first dose of the charged particle beam. The second dose measurement unit 33 is disposed in the beam transport line 13, and can measure the second dose of the charged particle beam. The response speed (response frequency) of the second dose measurement unit 33 is higher than the response speed (response frequency) of the first dose measurement unit 31. The first dose measurement unit 31 can measure the dose of the charged particle beam immediately before an irradiation target P is irradiated with the charged particle beam. On the other hand, the second dose measurement unit 33 can measure the dose of the charged particle beam in the beam transport line 13 at the response speed (response frequency) higher than that of the first dose measurement unit 31. In this manner, even in a case where the scanning irradiation is performed while scanning using the charged particle beam is performed at high speed, the second dose measurement unit 33 can measure the dose of the charged particle beam at high response speed. According to the above-described configuration, it is possible to measure the dose of the charged particle beam at high response speed even if the scanning irradiation is performed while the charged particle beam is used in scanning at high speed.

As the first dose measurement unit 31, the existing dose monitor used for the charged particle beam treatment apparatus in the related art can be employed, and the second dose measurement unit 33 can be additionally employed. A role can be divided into the first dose measurement unit 31 for low frequency and the second dose measurement unit 33 for high frequency. In this manner, it is possible to cope with fast scanning irradiation while the existing equipment is employed.

In the charged particle beam treatment apparatus 1 according to the present embodiment, the first dose measurement unit 31 and the second dose measurement unit 33 include the pair of electrodes 42 and 43 facing each other inside the space filled with gas, and the measurement unit 44 which measures the current generated between the pair of electrodes 42 and 43. The distance between the pair of electrodes 42 and 43 in the first dose measurement unit 31 is shorter than the distance between the pair of electrodes 42 and 43 in the second dose measurement unit 33. In this manner, a simple configuration which merely reduces the distance between the pair of electrodes 42 and 43 can increase the response frequency of the second dose measurement unit 33.

The charged particle beam treatment apparatus 1 according to the present embodiment further includes the low pass filter 34 that cuts the data relating to the frequency higher than the preset frequency from the data measured by the first dose measurement unit 31, the high pass filter 35 that cuts the data relating to the frequency lower than the preset frequency from the data measured by the second dose measurement unit 33, and the ion source control unit 36 that controls the operation of the ion source 32 which supplies the ion to the accelerator 11, based on the synthesized signal obtained by adding the signal output from the low pass filter 34 and the signal output from the high pass filter 35 to each other. In this manner, the first dose measurement unit 31 whose response speed (response frequency) is low uses the low pass filter 34, thereby enabling measurement accuracy to be improved in a low frequency region (region having low response speed). The second dose measurement unit 33 whose response speed (response frequency) is high uses the high pass filter 35, thereby enabling the measurement accuracy to be improved in a high frequency region (region having high response speed). The ion source control unit 36 controls the operation of the ion source 32, based on the synthesized signal obtained by adding the signal output from the low pass filter 34 and the signal output from the high pass filter 35 to each other. Therefore, the ion source control unit 36 can control the ion source 32, based on measurement results having the improved measurement accuracy in a wide range from the high frequency region to the low frequency region of the charged particle beam.

The second dose measurement unit 33 having fast response speed is newly installed, thereby enabling the dose to be measured at high response speed. However, in a case of the second dose measurement unit 33 having high response speed, the measurement accuracy is low in the low frequency region (region having low response speed). Consequently, there is a possibility that the measurement accuracy of the dose may be lowered. Therefore, the measurement result obtained by the second dose measurement unit 33 is filtered through the high pass filter 35, thereby cutting the signal in the low frequency region. The measurement result obtained by the first dose measurement unit 31 is filtered through the low pass filter 34, thereby cutting the signal in the high frequency region. In this manner, both of these are added to each other. That is, the low frequency region which is a weak point in the second dose measurement unit 33 is detected by the first dose measurement unit 31 side, thereby enabling the dose to be detected at high response speed without lowering the measurement accuracy.

The charged particle beam treatment apparatus 1 according to the present embodiment further includes the degrader 18 disposed in the beam transport line 13 so as to adjust the energy of the charged particle beam. The second dose measurement unit 33 is disposed on the upstream side from the degrader 18. In this manner, the second dose measurement unit 33 can measure the dose of the charged particle beam in a state of high energy before the charged particle beam is adjusted by the degrader 18. Therefore, the measurement accuracy of the second dose measurement unit 33 can be improved.

An embodiment of the invention is not limited to the above-described embodiment.

For example, in the present embodiment, the second dose measurement unit 33 is disposed on the most upstream side of the most upstream side in the electromagnet disposed in the beam transport line 13. Alternatively, for example, as located at a position indicated by "33A" in FIG. 1, the second dose measurement unit 33 may be disposed at a position on the downstream side from the electromagnet located on the most upstream side. For example, as located at a position indicated by "33B" in FIG. 1, the second dose measurement unit 33 may be disposed at a position on the downstream side from the degrader 18.

In the above-described embodiment, the ionization chamber is employed as the second dose measurement unit 33, similarly to the first dose measurement unit 31. However, any type of measuring instrument may be employed as long as the instrument can measure the dose. The first dose measurement unit 31 may employ a measuring instrument other than the ionization chamber.

In the above-described embodiment, the low pass filter 34 is disposed for the first dose measurement unit 31, and the high pass filter 35 is disposed for the second dose measurement unit 33. Alternatively, any one or both of the filters may be omitted.

In the above-described embodiment, although an example of using the raster-type scanning irradiation has been described, the spot-type scanning irradiation may be performed. However, in a case of using the spot-type scanning irradiation, when a certain spot is irradiated with the beam, the irradiation is performed by causing the beam to stay at the spot for a predetermined time. Any method may be employed as long as only an integrated value of the dose can be detected when the spot is irradiated with the beam. Accordingly, even in a case of fast irradiation, the response speed of detecting the dose detection may not be increased up to a certain level or higher in some cases. In contrast, in a case of the raster-type scanning irradiation, the irradiation is performed while the beam scanning is performed all the time. Accordingly, it is necessary to detect the dose all the time. Therefore, in a case where fast scanning irradiation is performed, it is necessary to detect the dose at high speed. In this regard, an advantageous effect of adopting the embodiments of the invention is greatly achieved.

Figure 5:
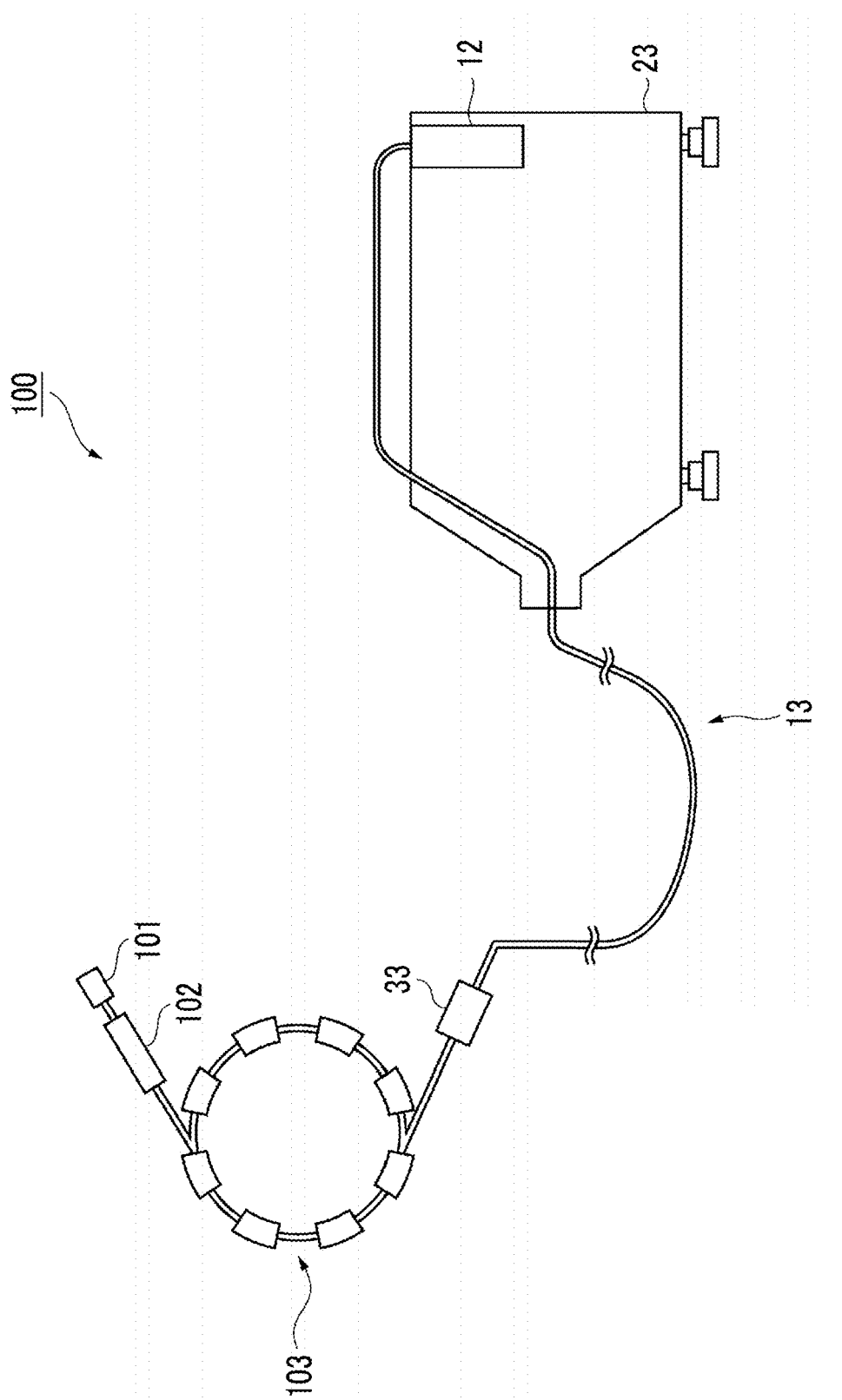
FIG. 5 is a schematic configuration diagram illustrating a charged particle beam irradiation apparatus according to a modification example.

As illustrated in FIG. 5, as the accelerator 11, a synchrotron may be adopted instead of the cyclotron. An ion source 101 and a linear accelerator 102 are disposed upstream of a synchrotron 103. Whereas the cyclotron has constant energy of the charged particle beam emitted therefrom, the synchrotron can change the energy of the charged particle beam emitted therefrom. Therefore, as illustrated in FIG. 5, in a case where the synchrotron is employed as the accelerator 11, the degrader 18 for adjusting the energy of the charged particle beam can be omitted from the charged particle beam treatment apparatus.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus comprising:
    an accelerator configured to emit a charged particle beam by accelerating a charged particle;
    an irradiation unit configured to irradiate an irradiation target with the charged particle beam;
    a beam transport line configured to transport the charged particle beam emitted from the accelerator, to the irradiation unit;
    a first dose measurement unit that is disposed inside the irradiation unit so as to measure a first dose of the charged particle beam; and
    a second dose measurement unit that is disposed in the beam transport line so as to measure a second dose of the charged particle beam,
    wherein a response frequency of the second dose measurement unit is higher than a response frequency of the first dose measurement unit.

2. The charged particle beam treatment apparatus according to claim 1,
    wherein the first dose measurement unit and the second dose measurement unit include
        a pair of electrodes facing each other inside a space filled with gas, and
        a measurement unit configured to measure a current generated between the pair of electrodes, and wherein a distance between the pair of electrodes in the first dose measurement unit is shorter than a distance between the pair of electrodes in the second dose measurement unit.

3. The charged particle beam treatment apparatus according to claim 1, further comprising:
a low pass filter configured to cut data relating to a frequency higher than a preset frequency from data measured by the first dose measurement unit;
a high pass filter configured to cut data relating to a frequency lower than the preset frequency from data measured by the second dose measurement unit; and
an ion source control unit configured to control an operation of an ion source which supplies an ion to the accelerator, based on a synthesized signal obtained by adding a signal output from the low pass filter and a signal output from the high pass filter to each other.

4. The charged particle beam treatment apparatus according to claim 1, further comprising:
an energy adjustment unit that is disposed in the beam transport line so as to adjust energy of the charged particle beam,
wherein the second dose measurement unit is disposed on an upstream side from the energy adjustment unit.

* * * * *